United States Patent [19]

Vincent et al.

[11] 4,148,912
[45] Apr. 10, 1979

[54] PHARMACEUTICAL COMPOSITIONS AND METHODS OF USING THE SAME

[75] Inventors: Michel Vincent, Bagneux; Georges Remond, Versailles; Xavier Pascaud, Paris, all of France

[73] Assignee: Science Union et Cie, Suresnes, France

[21] Appl. No.: 442,351

[22] Filed: Feb. 14, 1974

[30] Foreign Application Priority Data

Feb. 28, 1973 [FR] France ................................. 73.06993

[51] Int. Cl.$^2$ .................. A61K 31/295; A61K 31/29; A61K 31/205; A61K 31/195
[52] U.S. Cl. .................................... 424/295; 424/296; 424/316; 424/319
[58] Field of Search ................ 424/316, 319, 296, 295

[56] References Cited

U.S. PATENT DOCUMENTS 3,056,669  10/1962  Moyle et al. .......................... 71/115
3,646,121  2/1972  Ellenbogen et al. ............ 424/316 X

OTHER PUBLICATIONS

*Remington's Pharmaceutical Sciences*, 13th Ed., Mack Pub. Co., Easton, Penna./1965 p. 1201.

*Primary Examiner*—Frederick E. Waddell
*Attorney, Agent, or Firm*—Gordon W. Hueschen

[57] ABSTRACT

The present application relates to pharmaceutical compositions incorporating as active ingredient p.chlorohippuric acid or one of its mineral or organic base addition salts.

The pharmaceutical compositions are those adapted for parenteral or oral administration. They may include another active ingredient.

The present application also extends to therapeutic methods for using the said pharmaceutical compositions namely for protecting the gastric mucosa from acid hypersecretion, ulcers from therapeutic origin and for protecting the liver from toxic aggressions.

43 Claims, No Drawings

PHARMACEUTICAL COMPOSITIONS AND METHODS OF USING THE SAME

DESCRIPTION OF THE PRIOR ART

P. chlorohippuric acid has already been prepared for many years but is only known as a biological tool. It is the urinary excretion form of p.chlorobenzoic acid in some animals.

Moreover, p.chlorohippuric and its alkali-metal, lower alkylamine, alkanolamine and ammonium salts thereof have been disclosed in U.S. Pat. No. 3,056,669 as an agent able to modify the growth characteristics of plants.

SUMMARY OF THE INVENTION

The present invention relates to pharmaceutical compositions including as active ingredient p.chlorohippuric acid or a physiologically tolerable salt thereof with a mineral or organic base.

The pharmaceutical compositions are those which are suitable for parenteral or oral administration. They may include another active ingredient having similar, synergistic or complementary action, namely an antisecretory agent, an agent protecting the gastric mucose, a drug affecting the gastric motility or an anti-inflammatory drug.

The present invention also relates to a method of treating acid gastric hypersecretion without any action on the central nervous system which consist in administering to warm-blooded animals suffering from gastric hypersecretion, a safe but effective amount of p.chloro hippuric acid or a salt thereof with a mineral or organic base.

The present invention also extends to a method of protecting gastric mucosa which consists in administering to warm-blooded animals already suffering of ulceration of the gastric mucosa provoked by a gastric irritating drug, a safe but effective amount of p.chlorohippuric acid or a salt thereof with a mineral or organic base.

The present invention further relates to a method for protecting liver against toxic or bacterial aggressions by warm-blooded animals suffering from liver intoxications, which consists in administering a safe but effective amount of p.chlorohippuric acid or a salt thereof with a mineral or organic base.

The daily dosage, depending of the therapeutic use, ranges from 0.007 g/kg to 0.07 g/kg.

PREFERRED EMBODIMENTS

The present invention provides the pharmaceutical compositions containing as active principle at least p.chloro hippuric acid or one of its salts with a therapeutically suitable mineral or organic base, in admixture or conjunction with pharmaceutically acceptable inert carrier.

The pharmaceutical compositions of the present invention may be in a form adapted namely for oral or parenteral administration. They may, for example, be in the form of tablets, coated tablets, dragees, gelules, powders, aromatized powders or flavoured powders, drinkable suspensions or gels, drinkable or injectable solutions in phials or multidose flasks.

Among the addition salts with mineral bases, there may be especially mentioned alkali-metal salts such for example as potassium, ammonium or lithium salts; alkaline earth metal salts such as calcium salts; magnesium salts, neutral or basic aluminium salts, bismuth salts or ferrous salts.

Among the addition salts with organic bases, there may be especially mentioned the salts of aliphatic amines such as dimetylamine, trimethylamine, aminoethanol or tri-(hydroxymethyl) aminomethane; the salts of arylaliphatic amines such as benzylamine, dibenzylmethylamine, $\beta$-methyl phenylethylamine; the salts of betaines or quaternary ammoniums such as betaine or choline; the salts of natural or unnatural amino acids such as lysine, valine, ornithine, citrulline, glutamine or serine; the salts with guanidinic bases such as arginine, glycocyamine, agmatine or creatinine; the salts formed with polypeptides such as protamines, salmine, clupeine or caseine; the salts formed with aminosugars such as glucosamine, N-methyl glucamine or mannosamine.

The pharmaceutical compositions have beneficial therapeutic effects. Namely, they act on the acid gastric hypersecretion, they protect the gastric mucosa from irritations, ulcerations or pain caused either from gastric secretions or chemical disturbances. They have not any effect on the central nervous system. They have not any effect on the motility of the intestinal tract. They are particularly useful for treating patients suffering from disorders caused by the use of cortisonic or non steroidal anti-inflammatory compounds such as aspirine, phenyl butazone or arylalkanoic acids. The usual dosage varies from patient to patient depending of the age or the weight of the patient, the therapeutical indication or the nature of the disease. They ranges from 0.25 g to 1 g per unit dosage and from 0.5 g to 5 g daily.

The pharmaceutical compositions may include, besides p.chloro hippuric or a salt thereof, another active ingredient namely either a drug inhibiting the gastric secretions with an action of central origin such as atropine and its salts either a drug protecting the gastric mucosa such as gel of aluminium phosphate or aluminium pectate; either a drug possessing an antiemetic effect such as bietanautine or pipamazine, or a drug altering the gastric motility such as sulpiride. Further p.chlorohippuric acid or a salt thereof with a mineral or organic base may be incorporated into pharmaceutical compositions containing a drug able to affect the gastric mucosa namely salicylic acid derivatives, pyrazolone derivatives, anti-inflammatory aryl lower alkanoic acids, anti-inflammatory indolyl lower alkanoic acids, cortisone or prednidrugs which are known to request a constant survey of the gastric musoca by patients suffering from gastric disturbances or already having an ulcer.

The present invention extends further to a method of treating acid gastric hypersecretion without any action on the central nervous system which consists in administering to warm-blooded animals suffering from gastric hypersecretion, a non toxic effective amount of p.chlorohippuric acid or a mineral or organic base addition salt thereof.

The present invention extends further to a method of protecting the gastric mucosa by warm-blooded animals which consists in administering them an amount of p.chlorohippuric or a salt thereof efficient to relieve pain due to exulceration or to suppress hyperchlorhydria by patients suffering stomach disturbances.

The present invention still extends to a method for protecting liver cells from toxic damages due to chemical or bacterial poisoning which consists in administering to warm-blooded animals suffering from liver intoxications, a safe but efficient amount of p.chlorohippuric acid or a salt thereof with a mineral or organic base.

The following pharmacological tests show how the compounds of the present invention act on the gastric secretion without acting on central nervous system. They also show the low toxicity of the compounds of the present invention. Moreover, the compositions of the present invention have a protective effect on intoxicated liver.

The following examples illustrate the invention. They do not limit it in any way.

EXAMPLE 1

Sodium p.chloro hippurate

In a flask, there were successively added 150 g of glycine and 2000 ml of a 2 N sodium hydroxide solution. The reaction mixture was stirred till a clear solution was obtained, then cooled in an ice bath. 350 g of p.chlorobenzoyl chloride were added dropwise for 30 minutes through one hour while maintaining the temperature of the reaction mixture to 15° C. After the completion of the addition, the stirring was maintained for one hour at 15° C.

The temperature was then allowed to rise to 25° C., and stirring was maintained for 3 hours.

The insoluble matter was filtered off, then washed with water. The filtrate and the aqueous washings were acidified to pH 1 with concentrated hydrochloric acid. The precipitate was suction filtered off, washed with water till the washings be neutral, then washed with pentane. The so-obtained p.chloro hippuric acid was dried in a vacuum. After recrystallization from a mixture ethanol water, p.chloro hippuric acid melting at 144° C. was obtained, (Novello et als, J. Biol. Chem. 67, 555 (1926) gave 143° C.).

P.chloro hippuric acid was then suspended with five times its weight of water, and the mixture was rendered neutral by a careful addition of sodium carbonate. The so-formed sodium p.chloro hippurate was highly soluble in water. The aqueous solution was lyophilized, and there was obtained the theoretical amount of sodium p.chlorohippurate.

The latter product was hygroscopic.

Using the same procedure, potassium p.chlorohippurate and ammonium p.chlorohippurate were also obtained.

EXAMPLE 2

Basic aluminium p.chlorohippurate

A solution of sodium p.chlorohippurate was extemporaneously prepared by dissolving 21.3 g of p.chloro hippuric acid in 50 ml of a 2 N sodium hydroxide solution. There was added to this sodium p.chlorohippurate solution a solution formed with:
aluminium chloride hexahydrate: 8 g
water: 30 ml The mixture set quickly to a mass. The basic aluminium salt was filtered, suctioned off, washed with water then dried. There were obtained 20.5 g of basic aluminium p.chlorohippurate melting above 260° C.

| ANALYSIS : $C_{18}H_{15}Cl_2N_2O_7Al$ = 468.90 | | | |
|---|---|---|---|
| | C % | H % | N % |
| Calculated | 46.10 | 3.22 | 5.97 |
| Found | 46.25 | 3.46 | 5.88 |

Using the same procedure, calcium p.chlorohippurate and magnesium p.chlorohippurate were also obtained. These two salts were insoluble in water.

EXAMPLE 3

Basic bismuth p.chlorohippurate 97.2 g of bismuth nitrate (crystallized with 5 moles of water) were dissolved in 220 ml of acetic acid. There were added 6000 ml of water, then, while cooling, 500 ml of a concentrated solution of ammonia. Bismuth hydroxide precipitated. It was collected and washed by decantation with water until complete absence of nitrate ions in the washings. Bismuth hydroxide was suspended in 2000 ml of water then a micronised suspension of 16 g of p.chloro hippuric acid in 50 ml of water was added. The reaction mixture was then warmed on a water bath at 60°-65° C. for 90 minutes while stirring energetically. The mixture was allowed to cool, the precipitate was then filtered and suctioned off, washed with water and oven-dried. There were obtained 58 g of basic bismuth p.chlorohippurate crystallized with 3 moles of water.

ANALYSIS: $C_9H_8ClNO_9Bi_4$, $3H_2O$=1199.61; Percentage in p.chloro hippuric acid: Found: 17.47%; Calculated: 17.75%.

Using the same procedure and starting from extemporaneously prepared ferrous hydroxide, ferrous p.chlorohippurate was prepared.

EXAMPLE 4

L. ornithine p.chlorohippurate

Step A

Silver p.chlorohippurate 21.3 g p.chlorohippuric acid are dissolved in 50 ml 2 N sodium hydroxide solution. To this solution, 59.5 g of a concentrated silver nitrate solution made from:
Silver Nitrate: 40 g
Water: 100 g
are added under stirring.

The mixture becomes pasty and is diluted with 100 ml water. The stirring is kept for a further hour, keeping the bottle safe from the daylight. Thereafter, the reaction mixture is kept for 48 hours in a cool place.

The precipitate is filtered off, washed with water until the washings are free from nitrate ions. The wet precipitate weighing 90.1 g is further dried in an oven under vacuum. The yield in dry product is about 88%.

Silver p.chlorohippurate is used as such for the next step.

Step B 20.23 g of L.ornithine (hydrochloride) are dissolved in 200 ml water, then 38.46 g of silver p.chlorohippurate are added thereto portionwise. The last portions are carried away by adding 200 ml water. The mixture is kept under stirring for one hour, then filtered, succtionned off. The precipitate is washed with water until the washings are freed from chloride ions. The aqueous washings are united then evaporated off to dryness. 48.5 g of L.ornithine p.chlorohippurate are recovered. After drying under vaccuum until the weight remains constant, 36.3 g of dry L.ornithine p.chlorohippurate are obtained.

EXAMPLE 5

L.lysine p.chlorohippurate

Starting from 38.4 g silver p.chlorohippurate and 21.91 g. L.lysine monohydrochloride, 30.1 g of L.lysine p.chlorohippurate are obtained. The yield amounts to 70%.

EXAMPLE 6 dl.lysine p.chlorohippurate

In a cylinder of 100 ml, 21.37 g p.chlorohippuric acid and 30.6 g of an aqueous 47.8% solution of dl.lysine are mixed together. After keeping the mixture for one hour under stirring, the solvent is evaporated off under reduced pressure. 35.7 g of dl.lysine p.chlorohippurate are thus recovered. The yield amounts to 99.4%.

EXAMPLE 7

L.arginine p.chlorohippurate

A concentrated solution of L.arginine is made from 20 g L.arginine and 135 ml water. 127 g of this solution and 21.37 g p.chlorohippuric acid are mixed together. The whole mixture is stirred for one hour and thereafter evaporated off to dryness. The crude L.arginine p.chlorohippurate weighing 42.3 g is further purified. The crude product is taken up with 300 ml water. To this solution, arginine is added very carefully until the pH reaches the value of 7.2. The clear solution is then evaporated off. 32.7 g of L.arginine p.chlorohippurate are recovered and dried on phosphoric anhydride.

EXAMPLE 8

Pharmaceutical forms containing a compound of the present invention:

a) Tablets containing 0.400 g of p.chlorohippuric acid

| | |
|---|---|
| p.chlorohippuric acid | 400 g |
| lactose | 50 g |
| potatoes starch | 45 g |
| gelatin | 4 g |
| magnesium stearate | 1 g |

This mass was mixed and compressed to give 1000 tablets each weighing about 0.50 g.

b) Drinkable suspension

| | |
|---|---|
| basic aluminium p.chlorohippurate | 5 g |
| methyl p.hydroxybenzoate | 0.05 g |
| propyl p.hydroxybenzoate | 0.05 g |
| citric acid | 0.10 g |
| acid sodium phosphate | 0.15 g |
| glycerin | 10 g |
| carboxy methyl cellulose | 1.50 g |
| sugar | 25 g |
| vanillin | 0.01 g |
| colloidal silica | 1.50 g |
| distillated water q.s.p. | 100 g |

PHARMACOLOGICAL STUDY OF THE COMPOUNDS OF THE PRESENT INVENTION

(I) p. CHLOROHIPPURIC ACID

(A) Acute Toxicity

The acute toxicity was determined on lots of 6 to 10 male mice (strain CD) weighing from 25 to 30 g, kept in observation for a period of 8 days.

The average letal dose ($LD_{50}$) was determined according to the method of C. S. Weil:

by intraperitoneal route, the $LD_{50}$ is 1.43 (1.27–1.61) g/kg by oral route, the $LD_{50}$ is >4 g/kg.

The first letal dose was 1.50 g/kg, per orally, at the dose of 4 g/kg, 2/6 deaths were observed for the first hours following the treatment.

(B) Activity on the Gastric Secretion on the Rats (1) Rats (Shay)—4 hours (a) technical reminder:

The gastric secretions were collected 4 hours after the ligation of pylorus on male rats (strain S D) weighing from 250 to 275 g.

The determination of free acidity (pH=3.5) and total acidity (pH=8.5) was carried out with a titrated sodium hydroxide solution accurately titrated (about 0.01 N). The concentrations in ions $Na^+$ and $K^+$ were determined by a flame photometer.

p.chlorohippuric acid was administered by intraduodenal route just before the pylorus was ligated.

(b) results:

They were summarized in the following table.

TABLE I

| No. of rats | | Volume ml/4h/ 100g | pH | Free Acidity | | Total Acidity | | Sodium | | Potassium | |
|---|---|---|---|---|---|---|---|---|---|---|---|
| | | | | mEq/l | µEg/4h/ 100g | mEq/l | µEq/4h/ 100g | mEq/l | µEq/4h/ 100g | mEq/l | µEq/4h/ 100g |
| 15 | Control NaCl 0,14M 2 ml/kg | 2,79 ± 0,22 | 1,10 ± 0,02 | 91 ± 4 | 264 ± 29 | 115 ± 4 | 330 ± 35 | 29,3 ± 1,8 | 79 ± 5 | 12,8 ± 0,9 | 34,3 ± 2,3 |
| 5 | p.chloro hippuric acid 20 mg/kg | 2,10 ± 0,39 NS | 1,20 ± 0,07 NS | 76,1 ± 10 NS | 170 ± 47 NS | 101 ± 10 NS | 222 ± 56 NS | 46 ± 9,5 p<0,01 | 88 ± 12 NS | 11,7 ± 1,0 NS | 25,5 ± 6,5 NS |
| 15 | p.chloro hippuric acid 50 mg/kg | 1,94 ± 0,23 p<0,02 | 1,29 ± 0,07 p<0,05 | 71 ± 5 p<0,01 | 149 ± 24 p<0,01 | 106 ± 3 NS | 209 ± 27 p<0,01 | 34 ± 3,1 NS | 68 ± 7 NS | 14,2±5,2 NS | 29,7 ± 4,3 NS |
| 5 | p.chloro hippuric acid 80 mg/kg | 0,15 ± 0,07 p 0,001 | | | | | | | | | |

The values represent the average ± the standard deviation. The statistical analysis is realized with the STUDENT's test "t", with NS = no significant for p>0.05

At a dose ranged between 20 to 80 mg/kg I D, p.chloro hippuric acid inhibits significantly the gastric secretion on the rat (Shay)—4 hours. This inhibition, correlated with the doses, both concern the secretory volumes and the acid concentrations.

The concentrations in ions Na+ increase in a parallel way with the acid inhibition. The concentrations in ions K+ are not altered.

The average active dose ($ED_{50}$) concerning the inhibition of the output of the free acid is:

$ED_{50}$ (determined graphically): 36.2 mg/kg by intraduodenal route.

(2) Rat with a chronic gastric fistula

Male rats of C D strain, weighing about 300 g the beginning day were implanted surgically with a plastic canula in the fore stomach. They are allowed to rest for at least 15 days before they are tested for gastric secretion.

The days they are tested, the rats are fastened without any consistent food, 18 hours before the gastric secretions are collected. The stomach is then washed with physiological water and the rats rest for one hour.

(C) Effects on Experimental Ulcers (1) Restraint ulcer p.chlorohippuric at 100 mg/kg per os protects at 75% the fundec mucosa of the rats (strain L E) from exulceration caused by restraint.

The avery active dose calculated graphically is 76 mg/kg±12 by oral way.

(2) Ulcers and Gastric Haemorrhagias caused with Aspirin

Lots of 8 male rats (strain SD) weighing from 150 to 175 g received by oral way a single dosis of Aspirin (80 mg/kg). One hour before administration they received by oral way a suspension of p.chlorohippuric acid in a solution of arabic gum in water. The dosis administered ranged from 25 to 100 mg/kg and the number and the severity of the ulcers presented by each rat are noticed.

In this test p.chlorohippuric acid protects the rats from haemorrhagias and exulcerations. The average dosage which inhibits at 50% the heavy ulcers is 37.8 mg/kg per os.

(D) Effects on Gastric and Intestinal Motricities (a) Gastric motility:

Administered to the mice (CD Strain) per os p.chlorhippuric acid at dosis from 50 to 200 mg/kg has a slight but statistically significant curbing effect.

(b) Colic motility:

p.chlorohippuric acid at dosis ranging from 50 to 200 mg/kg on mice by oral way is without effect on the depletion of the colon.

(E) Effects on the Central Nervous System

The compound is without any anti-emetic property on dogs. It does not cause any effect on the behaviour. By the rats only the search interest seems to be affected but only for a very short period of time.

(F) Effects on Autonomic Nervous System p.chlorohippuric acid does not inhibit contractions provoked by Acetyl choline or Serotonine on the smooth muscles of the digestive tract. It is also without effect against the contracts of the rat duodenum caused by Baryum chloride.

(II) BASIC ALUMINIUM p.CHLOROHIPPURATE

The avery acute toxicity of said compound determined on mice by oral way cannot be determined. $LD_{50}$ is far higher than 2 g/kg. The toxic effect, if any, is delayed and the effects appear belatedly. At a dosis of 2 g/kg by oral way one death is noticed 72 hours after the administration.

The gastric secretion is largely decreased and $ED_{50}$ is about 75 mg/kg per intraduodenal way.

(III) BASIC BISMUTH p.CHLOROHIPPURATE

The latter is deprived of any acute toxic effect or neurologic effect for 5 days, even at a dosis of 4 g/kg per oral way.

Therefore the $LD_{50}$ is higher than 4 g/kg.

What we claim is:

1. A pharmaceutical composition useful for treating gastric hypersecretion including as active ingredient an amount of p-chloro hippuric acid or a physiologically tolerable salt thereof together with an inert non-toxic pharmaceutical carrier for oral or parenteral administration, in unit dosage form containing 0.25 gram to 1 gram per unit dosage.

2. The pharmaceutical composition of claim 1 wherein the active ingredient is p.chloro hippuric acid.

3. The pharmaceutical composition of claim 1 wherein the active ingredient is a salt of p.chloro hippuric with an alkali-metal base.

4. The pharmaceutical composition of claim 1 wherein the active ingredient is sodium p.chloro hippurate.

5. The pharmaceutical composition of claim 1 wherein the active ingredient is a salt of p.chloro hippuric acid with an earth alkaline metal.

6. The pharmaceutical composition of claim 1 wherein the active ingredient is a bismuth salt of p.chloro hippuric acid.

7. The pharmaceutical composition of claim 1 wherein the active ingredient is an aluminium salt of p.chlorohippuric acid.

8. The pharmaceutical composition of claim 7 wherein the aluminium salt is a basic aluminium salt.

9. The pharmaceutical composition of claim 1 wherein the active ingredient is a ferrous salt of p.chloro hippuric acid.

10. The pharmaceutical composition of claim 1 wherein the active ingredient is a salt of p.chloro hippuric acid with an organic base.

11. A pharmaceutical composition useful for treating gastric hypersecretion including as active ingredient an amount of a salt of p-chloro hippuric acid of the formula:

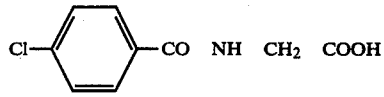

with an amino acid together with an inert non-toxic pharmaceutical carrier for oral or parenteral administration, which amount is effective when administered to warm-blooded animals for said purpose.

12. The pharmaceutical composition of claim 11 wherein the amino acid is unsubstituted or substituted with a guanidino, an ureido or an amino grouping.

13. The pharmaceutical composition of claim 12 wherein the amino acid is arginine, citrulline, ornithine or glycocyamine.

14. The pharmaceutical composition of claim 11 which includes another active ingredient possessing synergistic and/or complementary and/or similar activity.

15. The pharmaceutical composition of claim 14 wherein the further active ingredient is a compound endowed with antisecretory activity.

16. The pharmaceutical composition of claim 14 wherein the further active ingredient is a compound affecting the motility of the stomach.

17. The pharmaceutical composition of claim 14 wherein the further active ingredient is an anti-inflammatory active principle having a steroidal or a non-steroidal structure.

18. The pharmaceutical composition of claim 11 presented under a form adapted for oral or parenteral administration.

19. A method for treating acid gastric hypersecretion which consists in administering parenterally or orally to a warm-blooded animal suffering from gastric hypersecretion, an amount of p-chloro hippuric acid or a physiologically tolerable addition salt thereof, which amount is effective for said purpose.

20. The method of claim 19 wherein the effective amount of active ingredient ranges from 0.007 g/kg to 0.07 g/kg.

21. A method of protecting gastric mucosa which consists in administering parenterally or orally to a warm-blooded animal suffering from gastric distress due to hyperchlorhydria or from gastric pain due to ulcerations, an amount of p-chloro hippuric acid or a physiologically tolerable addition salt thereof, which amount is effective for said purpose.

22. The method of claim 21 wherein the effective amount of active ingredient ranges from 0.007 g/kg to 0.07 g/kg.

23. The pharmaceutical composition of claim 11 wherein the active ingredient is a salt of p.chloro hippuric acid with arginine.

24. The pharmaceutical composition of claim 11 wherein the active ingredient is a salt of p.chloro hippuric acid with citrulline.

25. The pharmaceutical composition of claim 11 wherein the active ingredient is a salt of p.chloro hippuric acid with ornithine.

26. The pharmaceutical composition of claim 11 wherein the active ingredient is a salt of p.chloro hippuric acid with glycocyamine.

27. The method of claim 20, in which the active ingredient is a salt of p.chloro hippuric acid with an organic base.

28. The method of claim 27, in which the organic base is an amino acid.

29. The method of claim 28, in which the amino acid is arginine.

30. The method of claim 28, in which the amino acid is citrulline.

31. The method of claim 28, in which the amino acid is ornithine.

32. The method of claim 28, in which the amino acid is glycocyamine.

33. The method of claim 22, in which the active ingredient is a salt of p.chloro hippuric acid with an organic base.

34. The method of claim 33, in which the organic base is an amino acid.

35. The method of claim 34, in which the amino acid is arginine.

36. The method of claim 34, in which the amino acid is citrulline.

37. The method of claim 34, in which the amino acid is ornithine.

38. The method of claim 34, in which the amino acid is glycocyamine.

39. A pharmaceutical composition according to claim 11, in unit dosage form containing 0.25 gram to 1 gram per unit dosage.

40. A pharmaceutical composition according to claim 11 wherein the active ingredient is a salt of p-chloro hippuric acid with an unsubstituted amino acid.

41. A pharmaceutical composition according to claim 11 wherein the active ingredient is a salt of p-chloro hippuric acid with a guanidinoamino acid.

42. A pharmaceutical composition according to claim 11 wherein the active ingredient is a salt of p-chloro hippuric acid with a ureidoamino acid.

43. A pharmaceutical composition according to claim 11 wherein the active ingredient is a salt of p-chloro hippuric acid with an amino amino acid.

* * * * *